(12) United States Patent
Fakhruddin

(10) Patent No.: US 7,978,342 B2
(45) Date of Patent: Jul. 12, 2011

(54) METHOD AND APPARATUS FOR MEASURING EXPANSION OF MATERIALS

(75) Inventor: Hasan Fakhruddin, Muncie, IN (US)

(73) Assignee: Ball State University Board of Trustees, Muncie, IN (US)

( * ) Notice: Subject to any disclaimer, the term of this patent is extended or adjusted under 35 U.S.C. 154(b) by 418 days.

(21) Appl. No.: 12/015,709

(22) Filed: Jan. 17, 2008

(65) Prior Publication Data

US 2008/0170236 A1      Jul. 17, 2008

Related U.S. Application Data

(60) Provisional application No. 60/885,295, filed on Jan. 17, 2007.

(51) Int. Cl.
   *G01B 9/02*      (2006.01)
   *G01N 25/16*     (2006.01)

(52) U.S. Cl. .......................... 356/521; 374/55

(58) Field of Classification Search ................ 356/35.5, 356/505, 521, 634; 359/232; 374/55, 187
   See application file for complete search history.

(56) References Cited

U.S. PATENT DOCUMENTS

| | | | |
|---|---|---|---|
| 2,351,572 A | 6/1944 | Kingston | |
| 2,546,796 A | 3/1951 | Swanson et al. | |
| 3,884,581 A * | 5/1975 | Pryor | 356/505 |
| 4,014,613 A * | 3/1977 | Sharpe et al. | 356/505 |
| 4,591,996 A | 5/1986 | Vachon | |
| 4,924,477 A | 5/1990 | Gilmore et al. | |
| 4,989,980 A | 2/1991 | Berg | |
| 5,121,987 A | 6/1992 | Berg | |
| 5,221,142 A | 6/1993 | Snow | |
| 5,231,285 A | 7/1993 | Berg | |
| 5,298,970 A | 3/1994 | Takamatsu et al. | |
| 5,362,151 A | 11/1994 | Ollivier et al. | |

(Continued)

FOREIGN PATENT DOCUMENTS

WO        9512802        5/1995

OTHER PUBLICATIONS

Hasan Fakhruddin, Quantitative Investigation of Thermal Expansion Using Single-Slit Diffraction, The Physics Teacher, 2006, pp. 47-49, vol. 44, The Indiana Academy for Science, and Humanities, Ball State University, Muncie, Indiana.

(Continued)

*Primary Examiner* — Michael A Lyons
(74) *Attorney, Agent, or Firm* — Daniel L. Boots; Bingham McHale LLP

(57) ABSTRACT

Methods for measuring expansion of a test sample. One method includes establishing a diffraction slit between two blades, with the position of at least one of the blades being dependent upon the length of a test sample of material. As the temperature of the sample changes, the width of the slit changes. Light is projected through the slit onto a target and an diffraction pattern is measured. Changes in the light diffraction pattern correspond to the thermal expansion of the sample. Another method includes establishing a diffraction slit between two blades, with the position of at least one of the blades being dependent upon a length along a test sample of material. As a load is applied to the test sample, the width of the slit changes. Changes in the light diffraction pattern correspond to Young's Modulus for the sample.

32 Claims, 5 Drawing Sheets

U.S. PATENT DOCUMENTS

| | | | |
|---|---|---|---|
| 5,479,261 A | | 12/1995 | Hansen |
| 5,870,195 A | * | 2/1999 | Sasan .......................... 356/499 |
| 6,687,011 B1 | * | 2/2004 | Lee et al. ..................... 356/480 |

OTHER PUBLICATIONS

S.S.R. Inbanathan, K. Moorthy, and G. Balasubramanian, Measurement and Demonstration of Thermal Expansion Coefficient, The Physics Teacher, Dec. 2007, pp. 566-567, vol. 45, Apparatus for Teaching Physics, Department of Physics & Astronomy, SUNY-Stony Brook, Stony Brook, NY.

R. Mostert, Classroom Experiments on Thermal Expansion of Solids, The Physics Teacher, Jan. 1992, p. 15, vol. 30, Vondelstraat 270, 1814 MC Alkmaar, The Netherlands.

Ricardo Trumper and Moshe Gelbman, Measurement of a Thermal Expansion Coefficient, The Physics Teacher, Oct. 1997, pp. 437-438, vol. 35, School of Education of the Kibbutz Movement, Haifa University, Israel, and Physics Project—Tomorrow 98, Hebrew University, Jerusalem.

Carl H. Hayn, Thermal Contraction and Stretching, The Physics Teacher, Jan. 1998, p. 14, vol. 36, Department of Physics, Santa Clara University, Santa Clara, CA.

Peter Insley, Chris Chiaverina and Jim Hicks, Doing physics—Physics activities for groups, The Physics Teacher, Nov. 1984, pp. 530-531, Department of Physics, Illinois Institute of Technology, Chicago, Illinois.

C.H. Blanchard, Thermal-expansion heat engine, The Physics Teacher, May 1983, p. 319, Department of Physics, University of Wisconsin, Madison, Wisconsin.

Hasan Fakhruddin, Thermal Expansion "Paradox", The Physics Teacher, Apr. 1993, p. 214, vol. 31, Indiana Academy for Science, Mathematics, and Humanities, Ball State University, Muncie, IN.

John D. Cutnell and Kenneth W. Johnson, Linear Thermal Expansion, Physics, 2004, pp. 341-348, Chapter 12, 6th Edition, John Wiley & Sons, Inc., Hoboken, NJ.

John D. Cutnell and Kenneth W. Johnson, Thin-Slit Diffraction, Physics, 2004, pp. 831-836, Chapter 27, 6th Edition, John Wiley & Sons, Inc., Hoboken, NJ.

Dilatometers and Thermal Expansion, Anter Corporation, http://www.anter.com, Jan. 23, 2006, Pittsburgh, PA.

PMIC (Precision Measurements and Instruments Corporation), http://www.pmiclab.com, Nov. 1, 2006, Corvallis, OR.

Theta Industries, Inc., http://theta-us.com, Nov. 1, 2006, Port Washington, NY.

National Physical Laboratory, http://www.npl.co.uk, Nov. 1, 2006, Middlesex, United Kingdom.

Orton Ceramic (USA), http://www.ortonceramic.com/industrial/testing.html, Nov. 1, 2006, Westerville, OH.

Vishay America, business-americas@vishay.com, Nov. 1, 2006, Shelton, CT.

\* cited by examiner

METHOD AND APPARATUS FOR MEASURING EXPANSION OF MATERIALS

FIELD

The claimed technology relates generally to measuring the expansion of materials and more specifically to a method and devices for accurately measuring the expansion of materials resulting from changes in temperature, mechanical stress, or other causes.

BACKGROUND

Materials may change their size and shape such as by expanding or contracting when subjected to various forces such as heat, mechanical stress, electricity, and the like. Most materials expand when heated, for example, and the amount and rate of this expansion must be considered when designing devices which will be subjected to temperature changes. The coefficient of linear thermal expansion represents the ratio of change of length to the actual (original) length per degree temperature change. Typically, this ratio is expressed as the fractional change in length of a material per degree of temperature change. Engineering and construction applications where temperature changes are expected must take the expansion and contraction of materials into account.

The coefficient of thermal expansion of a material can be measured with the use of a dilatometer. Dilatometers typically consist of a heat source, such as a furnace, and a means for measuring the expansion of the material being tested. Capacity dilatometers measure the expansion of a material using capacitor having one movable and/or flexible plate. Expansion of the material being tested moves the plate relative to the fixed plate thereby changing the capacitance of the capacitor. The change in capacitance is then used to calculate the change in distance between the capacitor's plates which is equal to the change in the length of the material being measured. Other dilatometers measure the expansion of the sample material using a strain gauge.

Most commercially available dilatometers are large and expensive pieces of equipment. Additionally, many are equipped with heat sources capable of reaching temperatures in excess of 1000° Celsius making them unsuitable for certain applications such as educational science labs. There remains a need for a less expensive but highly accurate means for determining the coefficient of thermal expansion of materials. Additionally, there is also a need for the ability to accurately measure very small changes in the size of materials when they are subjected to a variety of stresses other than temperature changes.

DESCRIPTION

Figure 1:
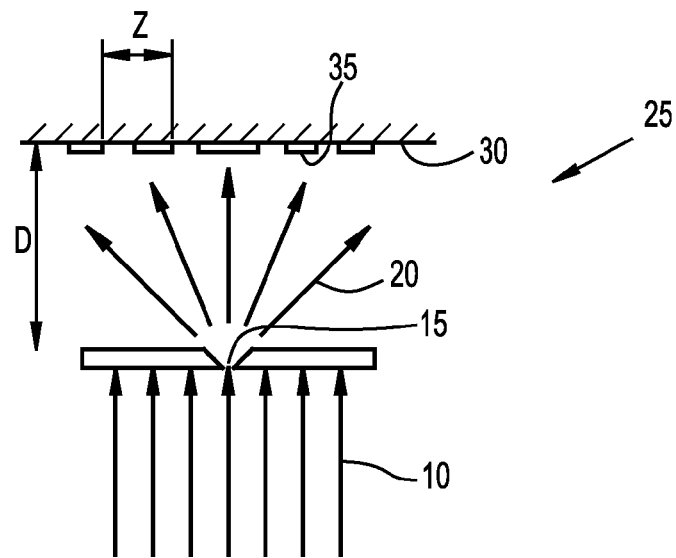
FIG. 1 is a schematic diagram of wave diffraction through a single slit.

For the purposes of promoting an understanding of the principles of the claimed technology and presenting its currently understood best mode of operation, reference will now be made to the embodiments illustrated in the drawings and specific language will be used to describe the same. It will nevertheless be understood that no limitation of the scope of the claimed technology is thereby intended, with such alterations and further modifications in the illustrated device and such further applications of the principles of the claimed technology as illustrated therein being contemplated as would normally occur to one skilled in the art to which the claimed technology relates.

The phenomenon of diffraction can be observed when waves pass through a narrow aperture. As shown in FIG. 1, one example of diffraction occurs when light 10 passes through a narrow opening 15 having a width w. In this and other drawings, width w is depicted as being relatively large for the sake of clarity. In practice, the actual slit width is typically very small. After the waves 10 pass through the opening 15, they behave as if there were a single point source at the location of the opening and form a semi-circular diffraction pattern of ripples. This configuration is known as single-slit diffraction 25. As the width of the slit w becomes smaller relative to the wavelength $\lambda$ of the light (i.e., w/$\lambda$ approaches zero) the opening behaves more like a point source and diffraction increases.

If the diffracted light 20 is projected onto a screen 30 which is at a distance D from the slit 15, an interference or diffraction pattern 35 is formed. Diffraction pattern 35 is shown in an exaggerated fashion as a series of blocks for the sake of clarity. The distance between repeating points in the diffraction pattern, or fringe width, is represented as z. The relationship between the fringe width, the distance between the slit and the screen D, the slit width w, and the wavelength $\lambda$ of light passing through the slit is expressed in the equation:

$$zw = \lambda D \qquad 1$$

When solved for w, this relationship can be used to calculate the width of an opening by measuring the fringe width z resulting from passing light of a known wavelength $\lambda$ through a slit at a known distance D from a screen.

$$w = \frac{\lambda D}{z} \qquad 2$$

Changes in the diffraction pattern observed as a change in the value of z result from very small changes in the width of the slit opening. Consequently, very accurate measurements of the expansion and/or contraction of a material can be made by relating the change in length of a sample material to changes in slit width and observing the diffraction patterns resulting from projecting light of a known wavelength through the slit and onto a screen.

The linear coefficient of thermal expansion α represents the ratio of change of length of a material with respect to a change in temperature and can be expressed as:

$$\alpha = \frac{1}{\ell} \cdot \frac{\ell - \ell_\circ}{T - T_\circ} \qquad 3$$

Where $l_\circ$ is the initial length of the material being measured at initial temperature $T_\circ$, and l is the length of the material being measured at temperature T.

Coupling the expansion of a sample material to changes in the width of a narrow slit through which light is passing can be used to measure the coefficient of thermal expansion of the sample material. That is, where $l-l_\circ$ is equal to the difference between two slit widths ($w-w_\circ$), changes in the diffraction pattern resulting from light of a known wavelength passing through the slit can be measured and used to calculate the coefficient of thermal expansion of the sample material. Where $l-l_\circ=w-w_\circ$, substituting single slit diffraction equation solved for w produces:

$$\ell - \ell_\circ = \frac{\lambda D}{z} - \frac{\lambda D}{z_\circ} \qquad 4$$

Where λ is the wavelength of the light, D is the distance between the screen and the slit, z is the fringe width resulting from slit width w and $z_\circ$ is the fringe width resulting from slit width $w_\circ$. Substituting the right hand side of this equation into the previous equation for calculating the coefficient of thermal expansion and simplifying results in:

$$\alpha = \frac{\lambda D}{\ell_\circ} \cdot \frac{\frac{1}{z} - \frac{1}{z_\circ}}{T - T_\circ} \qquad 5$$

This equation can be used to calculate the linear coefficient of thermal expansion α for a sample material.

Figure 2:
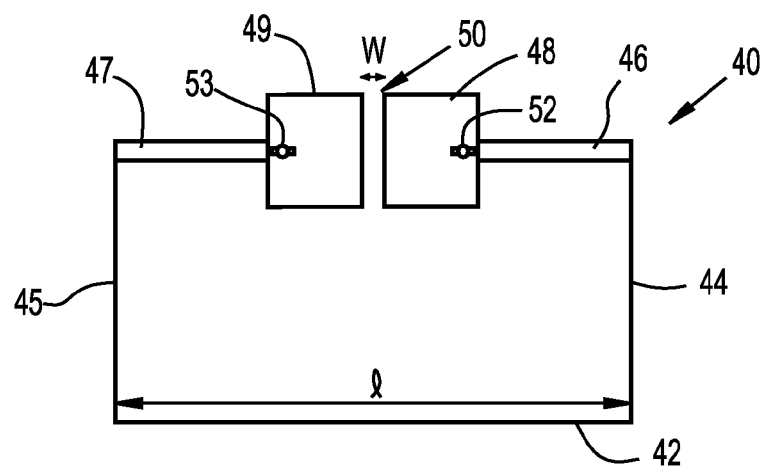
FIG. 2 is a front view of one embodiment of a device for measuring the thermal expansion of a material.

FIG. 2 shows one example of a device 40 for measuring the linear coefficient of thermal expansion of a sample material using changes in the diffraction pattern resulting from light passing through a narrow slit where changes in the width of the slit correspond to changes in the length of the sample material. Device 40 comprises a thin strip of the material to be tested 42 formed generally into a U shape having two substantially parallel arm portions 44, 45 and having a bottom portion of length t which is substantially perpendicular to arm portions 44, 45. Sample 42 may be bent, cast, molded, or otherwise suitably formed into the desired shape. Attached to each arm portion 44, 45 is a bracket 46, 47, respectively, which is substantially parallel to the bottom portion of sample 42. Brackets 46, 47 may be made out of wood, ceramic, plastic, glass, composite, alloy, or some other suitable material that has a relatively low coefficient of thermal expansion. Optionally, brackets 46, 47 are coated with a sealant, insulation, or other material to isolate them from moisture and changes in temperature.

A slit blade 48, 49 is adjustably mounted to each bracket 46, 47, respectively. The blades 48, 49 are configured and arranged so as to form a slit 50 having a uniform width w. In this particular example, each blade 48, 49 includes an adjustment screw 52, 53 which allows the width w of slit 50 to be adjusted as desired. The blades 48, 49 may be made of the same or different material as the brackets such as metal alloy, glass, ceramic, plastic, and the like. Optionally, blades 48, 49 are coated with a material which protects them from moisture and changes in temperature.

As the temperature of the sample material changes, any resulting changes in the length l of the bottom portion 42 of the material are reflected in changes in the width w of slit 50. For example, if the sample material is heated, bottom portion 42 will expand and increase in length. As the length of bottom portion 42 increases, arm portions 44, 45 are urged apart thereby moving brackets 46, 47 apart and increasing the width w of slit 50. Device 40 is configured so that the increase in the length of bottom portion 42 is equal to the increase in the width of slit 50, i.e., $l-l_\circ=w-w_\circ$. By passing light of a known wavelength λ through slit 50 before and after heating the sample, changes in the diffraction pattern can be measured to obtain values for the fringe width $z_\circ$ at the initial temperature $T_\circ$ as well as the fringe width z at the final temperature T. The initial length $l_\circ$ of bottom portion 42 and the distance D to the screen where the diffraction pattern is projected can be measured. Once these values are obtained, equation 5 can be used as previously discussed to obtain a value for the coefficient of thermal expansion of the sample material.

Alternatively, a series of measurements of fringe widths z can be taken at different temperatures and the results plotted on a graph. On a graph of the reciprocal of fringe width (1/z) plotted as a function of temperature T, the slope of a line is:

$$\text{Slope} = \frac{\alpha \ell_\circ}{\lambda D} \qquad 6$$

Solving this equation for the coefficient of thermal expansion α yields:

$$\alpha = \frac{(\text{Slope})\lambda D}{\ell_\circ} \qquad 7$$

By measuring the slope from the graph, an accurate value of α may be calculated. Optionally, the graphing and measurement may be automated using a microcomputer or similar device so that multiple measurements may be obtained quickly and the slope of a best-fit line from the resulting graph generated automatically.

Figure 3:
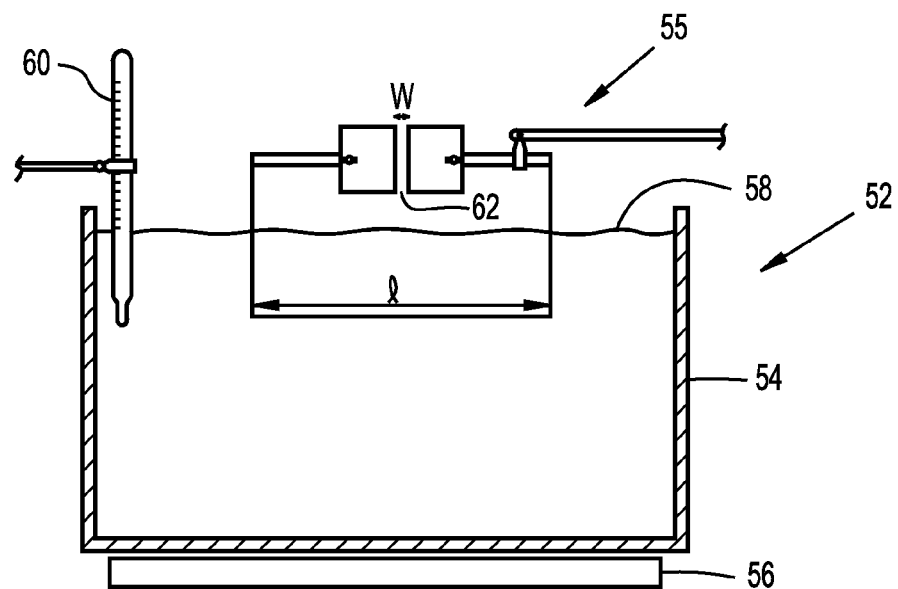
FIG. 3 is a partial cut away view of another embodiment of a device for measuring the thermal expansion of a material.

One example of an apparatus 52 for measuring the coefficient of thermal expansion of a material is shown in FIG. 3. In this particular example, a device 55 similar to that described in FIG. 2 is heated by immersing the device 55 in a water bath 58. The water bath comprises a tank 54 heated by means of a hotplate 56 and monitored using a thermometer 60. In other examples, the device may be heated using a furnace, oven, electrical resistance heater, or any other suitable heat source as desired and the temperature monitored using other monitoring means such as a thermocouple. Optionally, the water bath may be cooled rather than heated to measure the contraction of the sample material rather than the expansion. The water bath may be replaced by alcohol, ethylene glycol, or any other suitable substance having a freezing point lower than water if measurements below 0° Celsius are desired. Operation of apparatus 52 is similar to that previously described with respect to FIG. 2.

Figure 4:
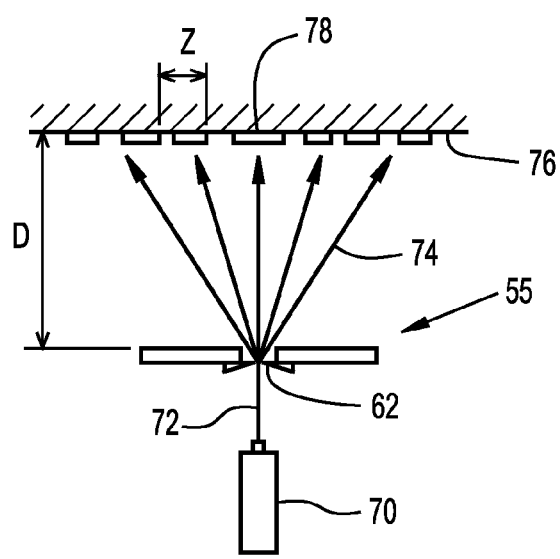
FIG. 4 is top plan view of the embodiment of the device shown in FIG. 3.
Figure 5:
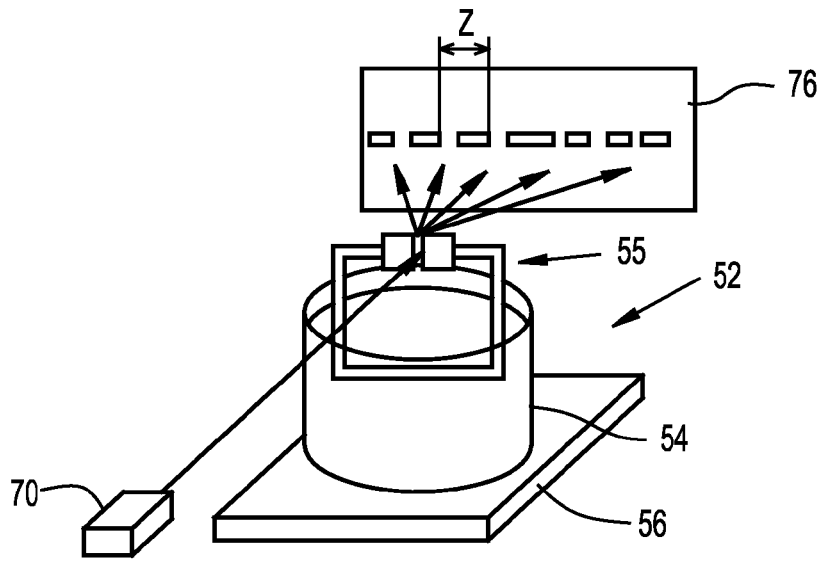
FIG. 5 is a perspective view of device shown in FIG. 3.

FIG. 4 is a top plan view of the apparatus 52 shown in FIG. 3. The water bath 58, tank 54, hotplate 56, and thermometer 60 have been omitted from this view for the sake of clarity. A light source having a known wavelength 70, in this particular example a laser, projects a beam of light 72 through the slit 62 of device 55. The light is diffracted and the diffracted light 74 strikes a screen 76 disposed at a known distance D from the slit 62. The resulting diffraction pattern 78 can be used to measure the fringe distance z and changes in the fringe distance caused by changes in the width w of slit 62 resulting from the expansion and/or contraction of the sample material used in device 55 can then be used to calculate the coefficient of thermal expansion of the sample material using the method and equations previously described. Apparatus 55 is shown in perspective in FIG. 5. Optionally, screen 76 further includes a scale or series of measuring marks inscribed or drawn on its surface to aide in the measurement of the fringe width z. In other embodiments, screen 76 is made of a photosensitive material or device which can automatically detect a diffraction pattern projected onto its surface and is operatively connected to a computer or other device such that the fringe distance z can be automatically measured and any changes in fringe distance automatically calculated.

Figure 6:
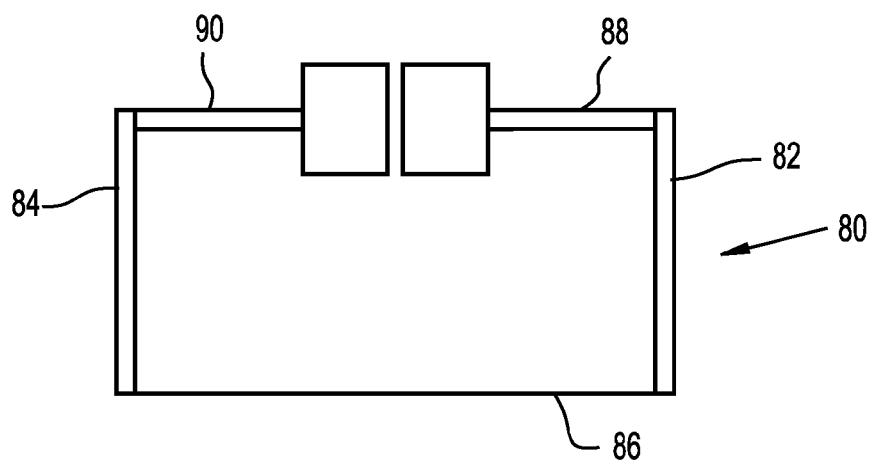
FIG. 6 is a front view of another embodiment of a device for measuring the thermal expansion of a material.

FIG. 6 is a front view of another embodiment of a device 80 for measuring changes in the length of a sample material. In this example, device 80 includes arm portions 82, 84 made of a material similar to or the same as the brackets 88, 90. In this particular example, only the bottom portion 86 of the device is made from the sample material. This particular configuration might be used when the sample material is a substance that is not easily bent, molded, or otherwise shaped into a suitable configuration other than a flat bar or rod.

Figure 7:
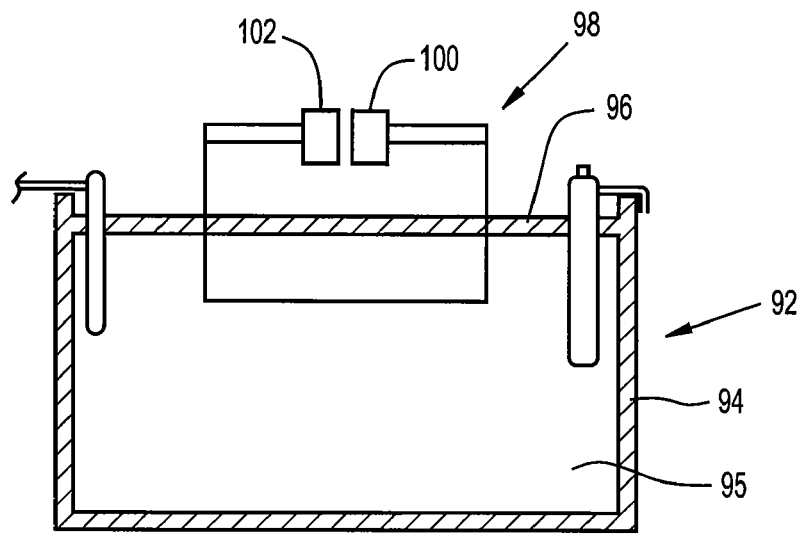
FIG. 7 is a partial cut away view of still another embodiment of a device for measuring the thermal expansion of a material.

Another example of an apparatus 92 is shown in FIG. 7. In this particular example, the liquid bath 95 used to heat the device 98 is contained in a tank 94 equipped with a lid 96. The lid 96 protects the slit blades 100, 102 of the device 98 from any deleterious effects caused by being directly exposed to heat or moisture from the liquid bath.

Figure 8:
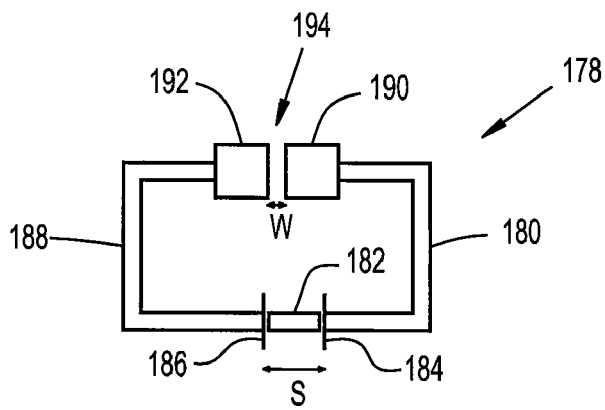
FIG. 8 is a front view of an embodiment of a device for measuring the expansion of a material.

FIG. 8 shows yet another device 178 suitable for measuring small changes in the length of a sample material 182 using the diffraction method and equations previously described. In this particular example, device 178 comprises a pair of movable brackets 180, 188, where each bracket includes a slit blade portion 190, 192, respectively, and a sample face portion 184, 186, respectively. The brackets are configured and arranged so that slit blades 190, 192 are disposed so as to form a slit 194 having a width w and sample face portions 184, 186 are disposed at a distance s from one another. The brackets are also configured and arranged so as to be freely moving and so that movement caused by a force exerted on the sample face portions 184, 186 is transmitted through the brackets and results in an equal movement of the slit blades 190, 192. That is, any change in the value of s results in an equal change in the value of w.

The disclosed method can be used to measure changes in length arising from causes other than heating. For example, the disclosed method can be used to measure the change in length in a sample material caused by an applied force which can be used to calculate Young's Modulus for the material. Young's Modulus is a measure of the stiffness of a material expressed as the ratio of the rate of change of stress to strain.

$$Y = \frac{F\ell_\circ}{A_\circ(\ell - \ell_\circ)} \qquad 8$$

Where Y is Young's Modulus, F is the applied force, $\ell_\circ$ is the original length of the object, $A_\circ$ is the original cross-sectional area of the object, and l is the length of the object under stress.

Figure 9:
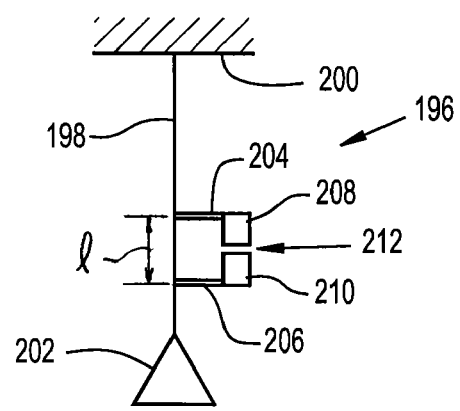
FIG. 9 is a front view of an embodiment of an apparatus for measuring the Young's Modulus of a material.

One example of a device which can be used to determine Young's Modulus is shown in FIG. 9. In this particular example, a wire 198 having a known cross-sectional area $A_\circ$ is attached to a surface 200. A weight 202 having a known mass is attached to the wire 198 opposite the surface 200. Attached at some point along the wire 198 are two brackets 204, 206 to which slit blades 208, 210, respectively, are mounted. The brackets 204, 206 and slit blades 208, 210 are configured so that a slit 212 of the desired width is created between the blades. Weight 202 applies a known force to wire 198 which causes a lengthening of the wire. This lengthening can be measured by observing changes in the diffraction patterns created by light of a known wavelength passing through slit 212 using the method previously described. The change in length ΔL of the wire 198 between brackets 204 and 206 can then be used to calculate the Young's Modulus Y of the wire. In other examples, devices according to the disclosed method for calculating the Young's Modulus of a material are configured so that the sample material is disposed generally horizontally and a force is applied using a mechanical means such as a screw, pneumatic piston, or the like rather than gravity.

Figure 10:
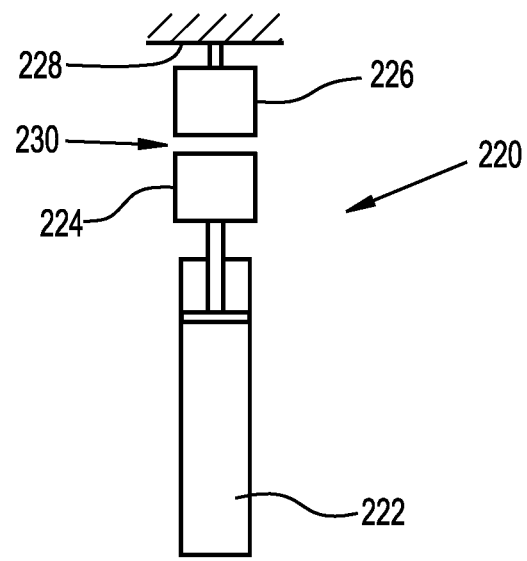
FIG. 10 is one embodiment of an apparatus for measuring the expansion of a liquid.

An example of a device 220 for measuring the expansion and/or contraction of a liquid is shown in FIG. 10. In this particular example, a sample liquid is placed in a piston 222 having a known volume. The piston 222 is operably connected to a slit blade 224, while a second slit blade 226 is fixably mounted to a surface 228. The piston 222 is configured and arranged so that the slit blades 224, 226 are disposed at a distance w thereby forming a slit 230. The piston 222 is then heated using a suitable heating means. As the liquid is heated and expands, the slit blades 224, 226 are urged closer together thereby decreasing w and causing changes to the diffraction pattern of light passing through the slit 230. The previously described method is particularly suited to measuring the very small changes in volume which result from heating most liquids.

Figure 11:
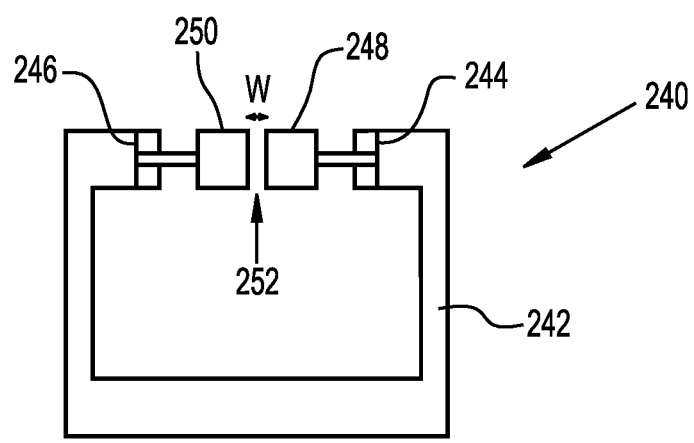
FIG. 11 is another embodiment of an apparatus for measuring the expansion of a liquid.

A dual piston arrangement of a device 240 for measuring changes in the volume of a liquid is shown in FIG. 11. In this example, a chamber 242 is equipped with two pistons 244, 246 which are operably connected to slit blades 248, 250, respectively, so that movement of the pistons results in corresponding movement of the slit blades. The chamber and pistons are configured and arranged so that the slit blades 248, 250 are disposed at a distance w from one another thereby forming a slit 252. The chamber 242 is filled with a sample liquid and then heated using a suitable heating means. As the liquid is heated and expands, the slit blades 248, 250, are urged closer together thereby decreasing w and causing changes to the diffraction pattern of light passing through the slit 252.

The preceding descriptions of devices represent a limited number of examples of using the disclosed method of measuring changes in the size of objects through changes in diffraction patterns. The disclosed method can easily be adapted to measure other types of small changes in the dimensions of materials using similar devices. In addition to thermal expansion, thermal contraction, and Young's Modulus previously discussed, changes in size caused by humidity (i.e., moisture expansion) as well as changes in size caused by the application of an electric current (i.e., piezoelectricity) could also be measured.

While the claimed technology has been illustrated and described in detail in the drawings and foregoing description, the same is to be considered as illustrative and not restrictive in character. It is understood that the embodiments have been shown and described in the foregoing specification in satisfaction of the best mode and enablement requirements. It is understood that one of ordinary skill in the art could readily make a nigh-infinite number of insubstantial changes and modifications to the above-described embodiments and that it would be impractical to attempt to describe all such embodiment variations in the present specification. Accordingly, it is understood that all changes and modifications that come within the spirit of the claimed technology are desired to be protected.

The invention claimed is:

1. A method for detecting thermal expansion of a sample, comprising:
   providing a sample having a length, and two members;
   linking the position of one of the members to the length of the sample;
   creating a constant width slit between the two members;
   projecting light through the slit and detecting a first diffraction pattern;
   heating the sample and changing the length after said detecting a first pattern;
   changing the width of the slit after said heating by said linking;
   projecting light through the changed slit and detecting a second diffraction pattern; and
   comparing the first diffraction pattern to the second diffraction pattern.

2. The method of claim 1 which further comprises calculating a coefficient of thermal expansion by said comparing.

3. The method of claim 1 wherein said heating is by immersing the sample in a liquid bath.

4. The method of claim 1 which further comprises thermally isolating the members from the sample.

5. The method of claim 1 which further comprises establishing thermal equilibrium in the sample and member before said detecting a first pattern.

6. The method of claim 1 which further comprises measuring the temperature of the sample.

7. The method of claim 1, further comprising:
   linking the position of the other of the two members to the length of the sample, wherein the two member are linked to opposing ends of the length.

8. The method of claim 1, wherein the two members are blades are configured and adapted to inhibit the formation of an interference pattern.

9. An apparatus for measuring a change in length of a material, comprising:
   a first blade having a first straight edge;
   a second blade having a second straight edge;
   a support structure for supporting said first edge parallel to and spaced apart from said second edge, wherein said first edge and said second edge form an open slit therebetween, at least one of said first blade or said second blade being movable relative to the other of said first blade or said second blade to vary the width of the slit, said support structure including a test section fabricated from the material and having a length
   a source of monochromatic light projecting through the slit; and
   a source of heat for changing the temperature of said test section;
   wherein said support structure and the one said blade are adapted and configured such that a change in the length of the test section during a change in temperature acts to vary the width of the slit.

10. The apparatus of claim 9 wherein the test section has two ends separated by the length, and the one of said first blade or said second blade is coupled to one end.

11. The apparatus of claim 10, wherein the other of said first or said second blade is coupled to the other end of the test section.

12. The apparatus of claim 9 wherein the length of the test section is generally parallel to the width of the slit.

13. The apparatus of claim 9 wherein the source of heat is a liquid bath.

14. The apparatus of claim 9 which further includes thermal insulation for isolating said source of heat from said first blade and said second blade.

15. The apparatus of claim 9 which further comprises a sensor for measuring the temperature of the test section.

16. The apparatus of claim 9 wherein the test section has a relatively constant cross section.

17. The apparatus of claim 9 wherein said support structure includes a piston movable within a cylinder, said piston supporting the one said blade, said sample being liquid within said cylinder, the wetted length of said cylinder being the length of said sample.

18. The apparatus of claim 9 wherein each said first blade and said second blade are movable relative to said support structure.

19. The apparatus of claim 9 which further comprises a target for receiving light projected through the slit, the projected light including a diffraction pattern formed when the monochromatic light passes through the slit.

20. The apparatus of claim 19, wherein the first and second blades are configured and adapted to inhibit the formation of an interference pattern at the target.

21. An apparatus for measuring a change in length of a sample, comprising:
   a sample having a length;
   a source of heat for changing the temperature of said sample;
   a first blade having a first straight edge;
   a second blade having a second straight edge;
   a support structure for supporting said first edge parallel to and spaced apart from said second edge, wherein said first edge and said second edge form an open slit therebetween, at least one of said first blade or said second blade being movable relative to the other of said first blade or said second blade to vary the width of the slit; and
   a source of monochromatic light projecting through the slit;
   wherein said support structure, said sample, and the one said blade are adapted and configured such that a change in the length of the sample during a change in temperature acts to vary the width of the slit.

22. The apparatus of claim 21 wherein the sample has two ends separated by the length, and the one of said first blade or said second blade is mechanically linked to one end.

23. The apparatus of claim 22, wherein the other of said first blade or said second blade is mechanically linked to the other end.

24. The apparatus of claim 21 wherein said support structure supports said sample such that the length of the sample is generally parallel to the width of the slit.

25. The apparatus of claim 21 wherein the source of heat is a liquid bath.

26. The apparatus of claim 21 which further includes thermal insulation for isolating said source of heat from said first blade and said second blade.

27. The apparatus of claim 21 which further comprises a sensor for measuring the temperature of the sample.

28. The apparatus of claim 21 wherein the sample has a relatively constant cross section.

29. The apparatus of claim 21 wherein said support structure includes a piston movable within a cylinder, said piston supporting the one said blade, said sample being liquid within said cylinder, the wetted length of said cylinder being the length of said sample.

30. The apparatus of claim 21 wherein each said first blade and said second blade are movable relative to said support structure.

31. The apparatus of claim 21 which further comprises a target for receiving light projected through the slit, the projected light including a diffraction pattern.

32. The apparatus of claim 21, wherein the first and second blades are configured and adapted to inhibit the formation of an interference pattern.

\* \* \* \* \*